US008979539B1

(12) United States Patent
Snyder

(10) Patent No.: US 8,979,539 B1
(45) Date of Patent: Mar. 17, 2015

(54) HYDRATION LEVEL MEASUREMENT SYSTEM AND METHOD

(75) Inventor: Seth Snyder, Providence, RI (US)

(73) Assignee: Humana Inc., Louisville, KY (US)

( * ) Notice: Subject to any disclaimer, the term of this patent is extended or adjusted under 35 U.S.C. 154(b) by 556 days.

(21) Appl. No.: 13/004,578

(22) Filed: Jan. 11, 2011

Related U.S. Application Data

(60) Provisional application No. 61/293,833, filed on Jan. 11, 2010.

(51) Int. Cl.
*G09B 19/00* (2006.01)
*G06F 19/00* (2011.01)

(52) U.S. Cl.
CPC ........ *G09B 19/0092* (2013.01); *G06F 19/3475* (2013.01); *Y10S 128/921* (2013.01)
USPC ............................ 434/236; 434/127; 128/921

(58) Field of Classification Search
CPC . G06F 19/3475; G06Q 50/22; G09B 19/0092
USPC ................. 128/921; 235/94 R; 426/231, 232; 434/127, 236, 238; 600/307
See application file for complete search history.

(56) References Cited

U.S. PATENT DOCUMENTS

| | | | |
|---|---|---|---|
| 8,176,948 B2 * | 5/2012 | Carrig | 141/21 |
| 8,378,830 B2 * | 2/2013 | Moran | 340/573.1 |
| 2002/0129663 A1 * | 9/2002 | Hoyt et al. | 73/861.79 |
| 2004/0131997 A1 * | 7/2004 | McGuire et al. | 434/127 |
| 2005/0113649 A1 * | 5/2005 | Bergantino | 600/300 |
| 2006/0036395 A1 * | 2/2006 | Shaya et al. | 702/127 |
| 2007/0048224 A1 * | 3/2007 | Howell et al. | 424/9.1 |
| 2007/0222619 A1 * | 9/2007 | Moran | 340/573.1 |
| 2008/0077489 A1 * | 3/2008 | Gilley et al. | 705/14 |
| 2009/0105560 A1 * | 4/2009 | Solomon | 600/301 |
| 2009/0234916 A1 * | 9/2009 | Cosentino et al. | 709/203 |
| 2010/0182518 A1 * | 7/2010 | Kirmse et al. | 348/836 |
| 2011/0236862 A1 * | 9/2011 | Culver et al. | 434/127 |
| 2012/0103926 A1 * | 5/2012 | Ibsies | 215/228 |
| 2012/0245439 A1 * | 9/2012 | Andre et al. | 600/310 |
| 2012/0299731 A1 * | 11/2012 | Triener | 340/573.1 |

* cited by examiner

*Primary Examiner* — Sam Yao
*Assistant Examiner* — Michael Humphrey
(74) *Attorney, Agent, or Firm* — Standley Law Group LLP

(57) ABSTRACT

A hydration level measurement system and method comprising a technology embedded scale that rewards individuals for drinking an appropriate amount of liquid throughout the day. In an example embodiment, a reusable water bottle is equipped with an RFID tag and assigned to an individual so that the user's hydration level may be tracked. The RFID tag logs the individual's access as well as "before-filling" and "after-filling" weights of the bottle when placed on the scale. A computer screen acknowledges the bottle's owner, and then indicates the increased weight and how many points will be awarded to the user using an ounces-to-points conversion. Data may be transferred from the scale computer to a web server and aggregated at the server from multiple scales for multiple "hydration challenges." A web application receives and processes user requests to display data related to each hydration challenge such as the current scores of the participants.

14 Claims, 8 Drawing Sheets

HYDRATION LEVEL MEASUREMENT SYSTEM AND METHOD

CROSS-REFERENCE TO RELATED APPLICATION

This application claims priority to U.S. Provisional Patent Application Ser. No. 61/293,833, filed Jan. 11, 2010, titled Hydration Level Measurement System and Method, the content of which is incorporated herein by reference.

BACKGROUND

Water is the most abundant component of the body. It is used in nearly all bio-chemical reactions so it is essential that an individual replace the water that is used by the body for such activities as regulation of body temperature as well as other bodily processes that contribute to a healthy life. Maintaining a proper level of hydration is essential to healthy living. Although proper hydration is important for maintaining healthy living, many individuals do not know how much water they consume or whether they are consuming an appropriate level of liquids. Therefore, there is a need for a system and method for easily determining an individual's level of liquid consumption and motivating an individual to maintain an appropriate level of liquid consumption. There is a need for a system and method that allows individuals to track how much water they are consuming while creating goals to motivate them to stay hydrated throughout the day.

SUMMARY

The present disclosure describes a technology embedded scale that rewards individuals for drinking an appropriate amount of water or other liquid throughout the day. In an example embodiment, a reusable water bottle or other drinking vessel is equipped with an RFID tag. The bottle is assigned to an individual so that the user's hydration level may be tracked using the RFID tag. The RFID tag logs the individual's access as well as "before-filling" and "after-filling" weights of the bottle when they place it on the scale. The user's name and the bottle weight information appear on a display at the scale.

The system and method supports users placing an RFID-tagged reusable bottle onto the scale and filling it with a liquid from a pitcher, a water jug, or any other type of liquid container. The scale is connected to a computer that registers each user interaction with the scale. As a user fills a bottle, a computer screen acknowledges the bottle's owner, and then indicates the increased weight and how many points will be awarded the user using a simple ounces-to-points conversion. Data may be transferred from the scale computer to a web server. Data may be aggregated at the server from multiple scales. A web site application receives and processes user requests to display data related to the hydration challenge such as the current scores of the participants.

DETAILED DESCRIPTION

Figure 1:
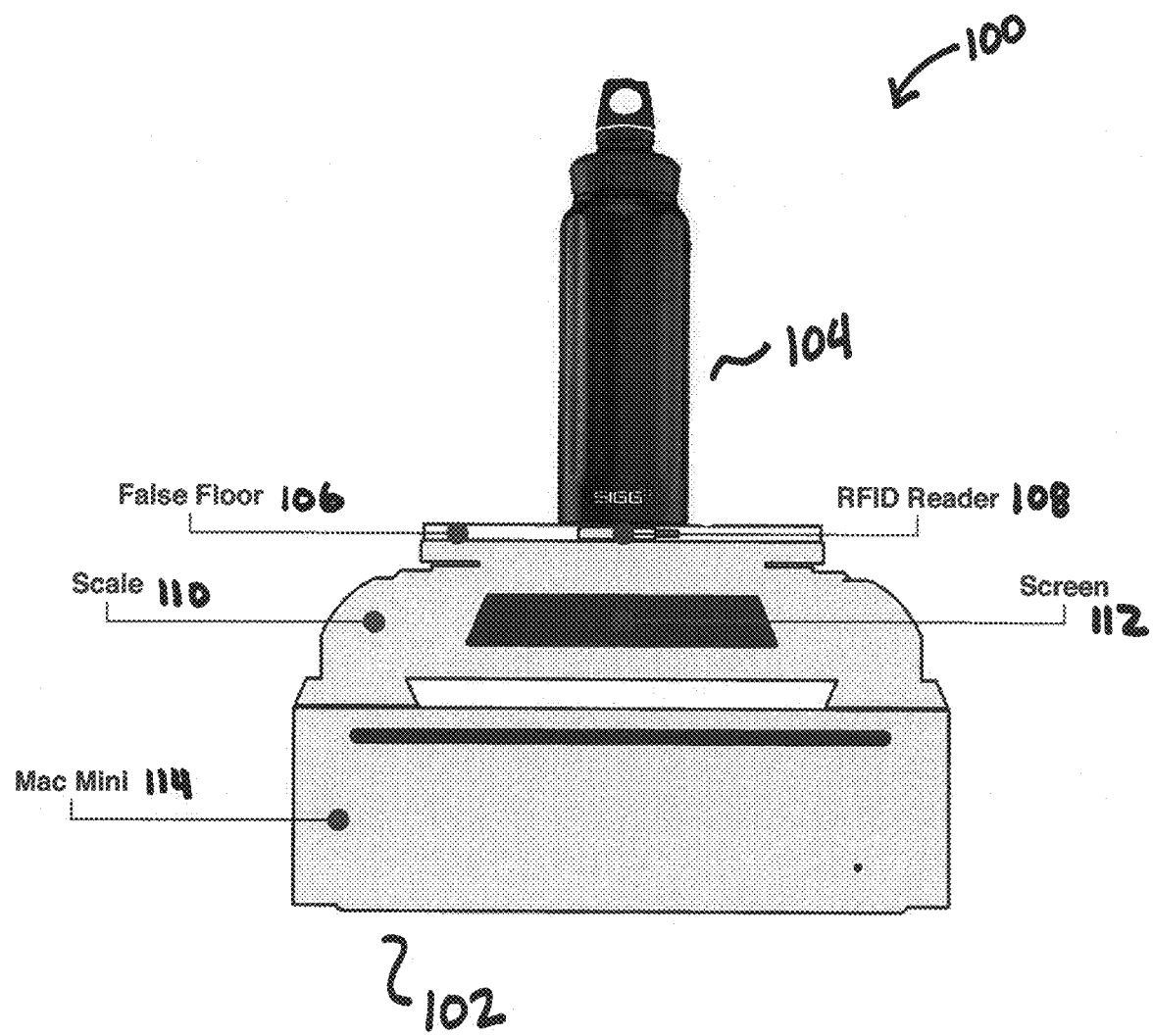
FIG. 1 is a component diagram of a bottle-weighing scale system according to an example embodiment.

Referring to FIG. 1, a component diagram of a bottle-weighing scale system according to an example embodiment is shown. In an example embodiment, the bottle-weighing scale system 100 comprises a bottle 104 or other type of drinking vessel with an attached or embedded RFID tag or other type of electronic identifier. The system base 102 comprises a scale 110 for weighing the bottle 104 and a computer 114 for receiving weight and other data from the scale and transferring it to a web server. The scale 110 is equipped with a false floor 106 that houses an RFID reader 108 or other type of device for detecting an electronic identifier. The scale 110 further comprises a screen 112 for displaying data related to a user's interaction with the scale. In an example embodiment, the computer 114 is an Apple® Mac Mini.

Figure 2:
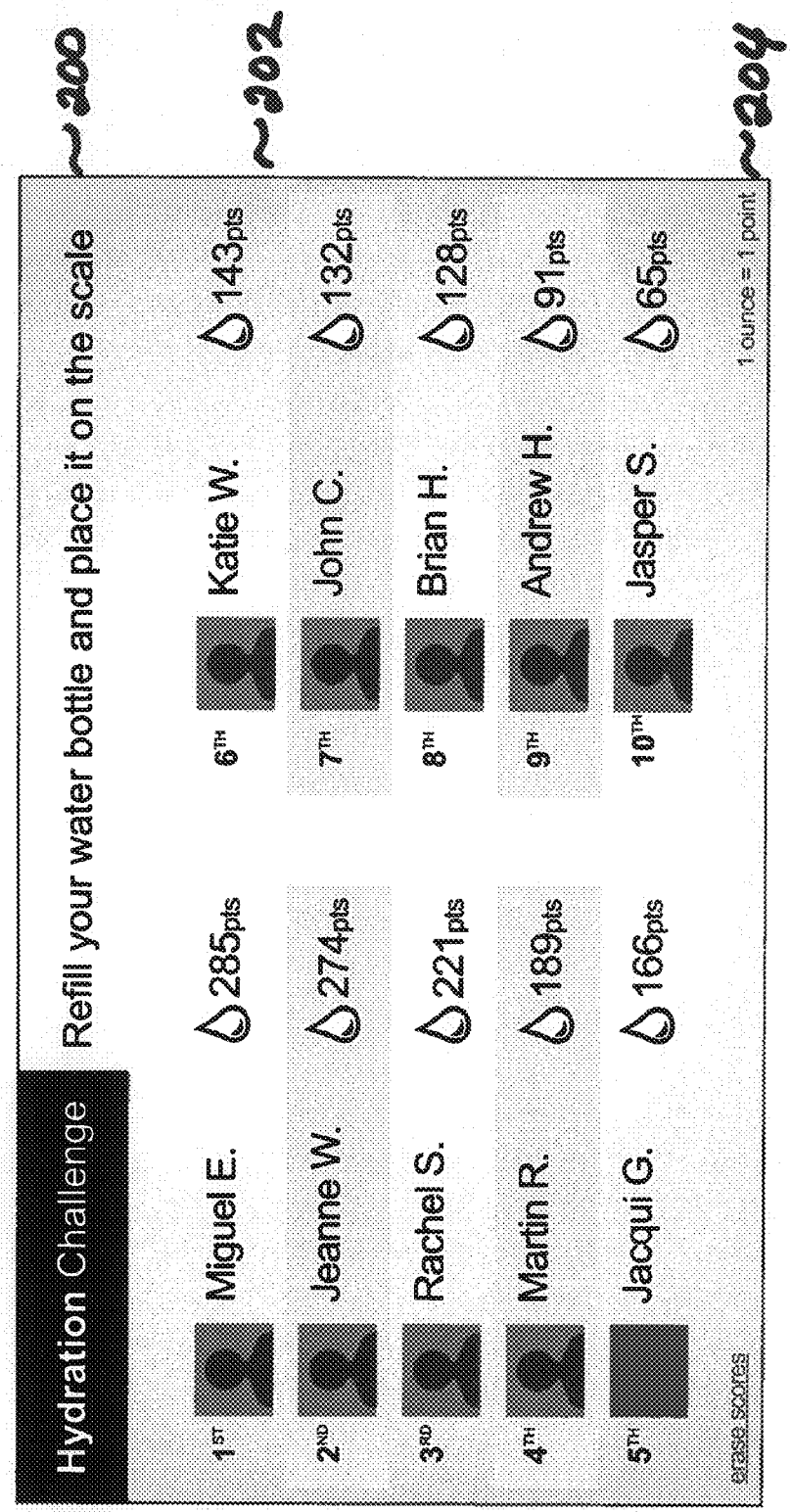
FIGS. 2-8 are sample screens for a computer application according to an example embodiment.

In an example embodiment, the user experience is as follows. Initially, the user places an empty bottle on the scale 110 of the system base 102. The RFID reader 108 scans the tag on the underside of the bottle. The computer screen 112 displays a "welcome user" message to acknowledge a successful scan. Referring to FIG. 2, a sample "fill bottle" screen according to an example embodiment is shown. In a top portion of the computer screen, a message is displayed to instruct the user to fill the bottle and place it on the scale 200. The screen may further display the names and point totals of other participants in the "hydration challenge" 202. Finally, a point conversion indicator 204 may be displayed at the bottom of the screen.

Figure 3:

Referring to FIG. 3, a sample "identifying" screen according to an example embodiment is shown. While the RFID read scans the tag on the underside of the bottle and determines the identity of the user, an "identifying" message is displayed to the user to indicate that the computer is performing an operation.

Figure 4:
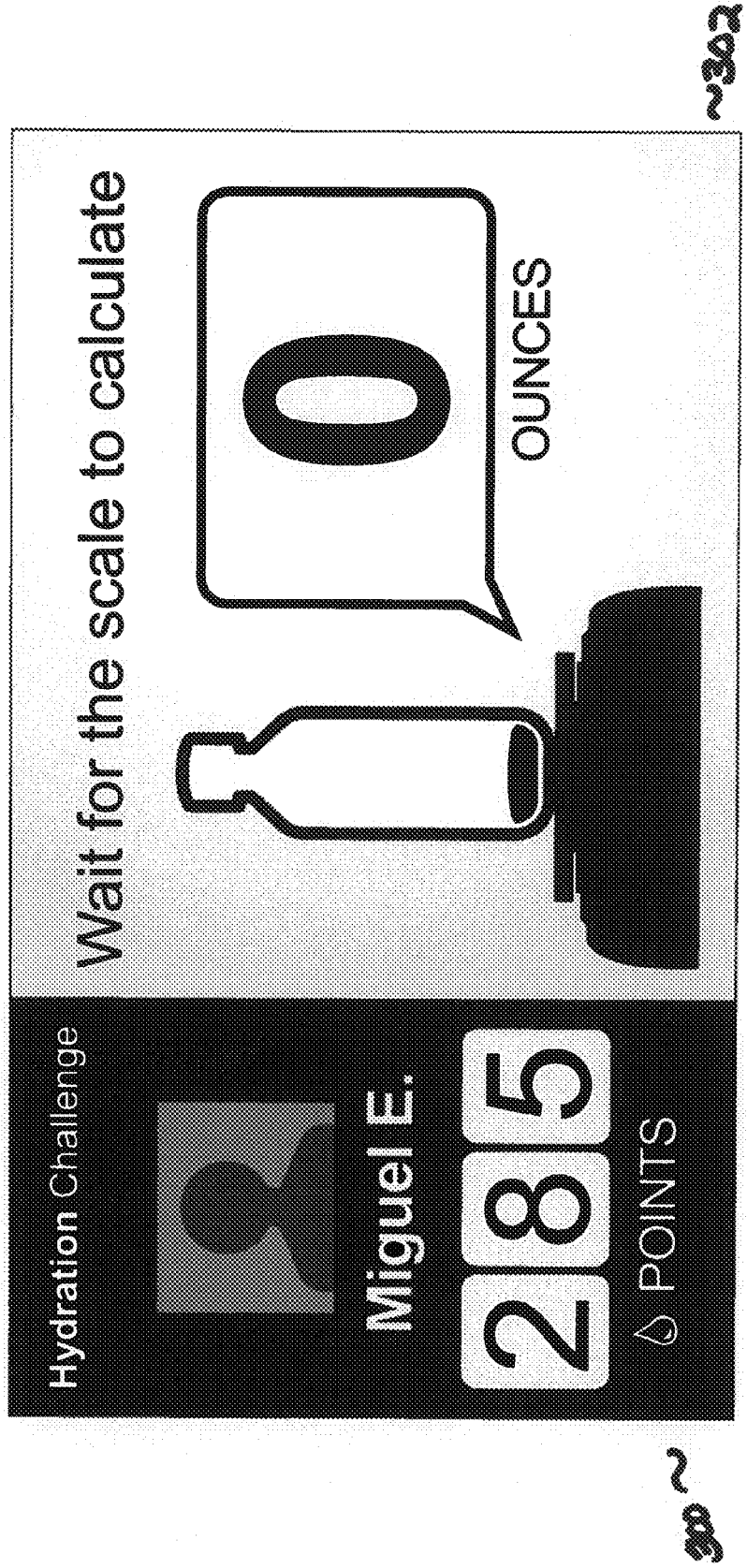

Referring to FIG. 4, a sample "wait" screen according to an example embodiment is shown. A successful scan of the RFID tag is acknowledged by displaying on the screen the user's name and other identifying information (e.g., picture) and the user's current point total 300. A wait message 302 (e.g., "wait for scale to calculate") may be displayed to the user to indicate that the computer is performing an operation.

Figure 5:

Referring to FIG. 5, a sample "weighing" screen according to an example embodiment is shown. The message indicates to the user that the computer is performing an operation.

Figure 6:

Referring to FIG. 6, a sample "remove" screen according to an example embodiment is shown. After the scale completes the weighing operation, the final weight is displayed 400 and the user is instructed to remove the bottle from the scale. In an example embodiment, the weight is displayed in ounces. Other measurements such as cups, milligrams, grams, etc. may be used.

Figure 7:
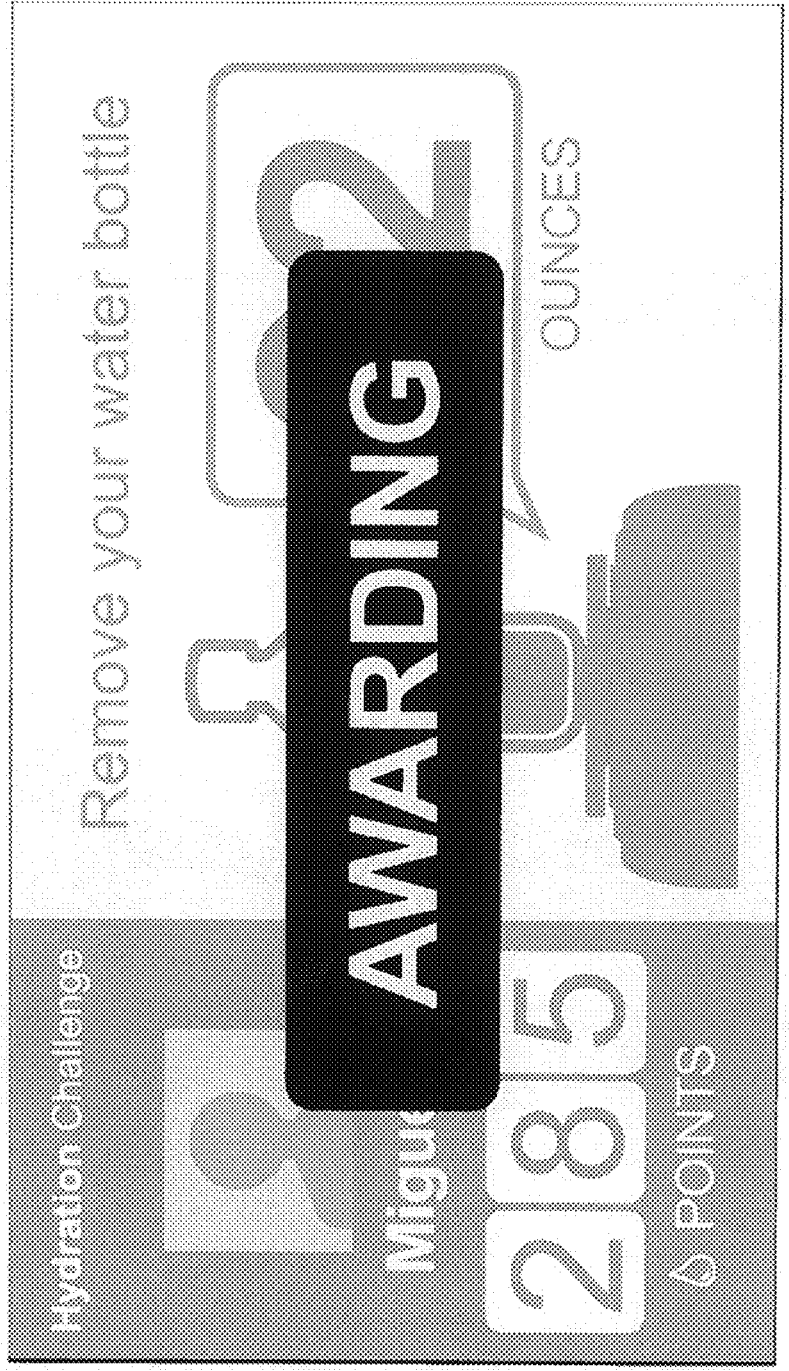

Referring to FIG. 7, a sample "award" screen according to an example embodiment is shown. When the user removes the bottle from the scale, the computer proceeds to add points to the user's point total. The message indicates to the user that the computer is performing an operation.

Figure 8:

Referring to FIG. 8, a sample "points awarded" screen according to an example embodiment is shown. In an example embodiment, one point is awarded for each ounce of liquid determined to be in the bottle 502. The point is added to the user's total and the user's new point total is also displayed 500. In an example embodiment, the screen is displayed for a set amount of time or until another user scans a bottle at the scale system. If the specified amount of time expires before another user scans a bottle, a welcome screen or other type of screen may be displayed.

User data collected at the scale may be transmitted from the computer to a web server using an Internet connection. Participants may access a browser-based application at the web server to see how others are performing in the "hydration challenge." A plurality of scales may be installed at one or more locations or facilities to increase the number of participants in a single challenge. Each "challenge" may be assigned an identifier that is used to track the individual participants in the challenge. Identifiers for individuals may be assigned to a challenge identifier to create a group of participants for a challenge. Each challenge may also have a start and end date to establish a time period for the challenge. During the challenge time period, the web application may report aggregated user totals across numerous locations or facilities. The user with the greatest number of points on the challenge end date may be declared the "hydration challenge" winner. The reporting of aggregated data and the declaration of a winner may help to increase the level of competition among the participants and cause them to more closely monitor their intake of liquids.

In other embodiments of a hydration level measurement system, a device that detects liquid volume rather than weight may be used. Such a device may use imaging techniques to detect volume changes in a bottle or other drinking vessel. Once a measurement is obtained, the measurement may be converted to points as explained above and the user's point total may be increased in relation to the liquid measurement. Any measurement device that is capable of measuring the liquid in a liquid containing vessel may be used. In addition, any liquid containing vessels capable of having an attached or associated identifier may be used.

A computerized hydration challenge system and method is described in reference to the appended figures. The description with reference to figures is made to exemplify the disclosed computerized system and method and is not intended to limit the system and method to the representations in the figures. From the foregoing description, it can be understood that there are various ways to construct a scale for measuring hydration and awarding points related to hydration levels while still falling within the scope of the present invention. In addition, various types of bottles or drinking vessels as well as attached or associated electronic identifiers may be used and fall within the scope of the present invention. As such, while certain embodiments of the present invention are described in detail above, the scope of the invention is not to be considered limited by such disclosure, and modifications are possible without departing from the spirit of the invention as evidenced by the following claims:

What is claimed is:

1. A hydration level measurement system comprising:
   (a) a measuring device comprising a vessel identifier detecting device;
   (b) a liquid containing vessel comprising a vessel identifier;
   (c) a computer connected to said measuring device for:
      (1) receiving a first reading of said vessel identifier from said vessel identifier detecting device;
      (2) receiving a first weight for said vessel identifier registered by said measuring device when said liquid containing vessel is empty;
      (3) storing said first weight in association with said vessel identifier;
      (4) receiving a second reading of said vessel identifier from said vessel identifier detecting device;
      (5) receiving a second weight for said vessel identifier registered by said measuring device when said liquid containing vessel is filled and is placed on said measuring device;
      (6) calculating a point value based on a difference between said second weight and said first weight;
      (7) receiving a user identifier associated with said vessel identifier;
      (8) combining said calculated point value with a previously stored total point value associated with said user identifier to calculate a total point value for said user identifier;
      (9) storing said total point value for said user identifier;
   (d) a display in electronic communication with said computer for displaying:
      (1) on a first screen:
         (i) user identifiers for a group of participants assigned to a challenge identifier; and
         (ii) a challenge point total for each participant assigned to said challenge identifier; and
      (2) on a second screen: in response to receiving said total point value for said user identifier, said user identifier and said total point value.

2. The hydration level measurement system of claim 1 wherein said measuring device is a scale.

3. The hydration level measurement system of claim 1 wherein said vessel identifier is an RFID tag.

4. The hydration level measurement system of claim 1 wherein said difference between said second weight and said first weight is measured in units selected from the group consisting of ounces, cups, milligrams, and grams.

5. A hydration level measurement method comprising:
   (a) receiving at a computer from a vessel identifier detecting device a first reading of a vessel identifier for an empty liquid containing vessel;
   (b) receiving at said computer a first weight for said vessel identifier registered by a measuring device for said empty liquid containing vessel;
   (c) storing at said computer said first weight in association with said vessel identifier;
   (d) receiving at said computer a second reading of said vessel identifier from said vessel identifier detecting device;
   (e) receiving at said computer a second weight for said vessel identifier registered by said measuring device when said liquid containing vessel is filled and is placed on said measuring device;
   (f) calculating at said computer a point value based on a difference between said second weight and said first weight;
   (g) receiving at said computer a user identifier associated with said vessel identifier;
   (h) combining at said computer said calculated point value with a previously stored total point value associated with said user identifier to calculate a total point value for said user identifier;
   (i) storing at said computer said total point value for said user identifier;
   (j) receiving at said computer at least one challenge identifier identifying a group of participants;
   (k) receiving at said computer a plurality of user identifiers assigned to said at least one challenge identifier;
   (l) displaying at said computer:
      (1) on a first screen:
         (i) user identifiers for said group of participants assigned to said challenge identifier; and
         (ii) a challenge point total for each participant assigned to said challenge identifier; and
      (2) on a second screen: in response to receiving said total point value for said user identifier, said user identifier and said total point value.

6. The hydration level measurement method of claim 5 wherein said measuring device is a scale.

7. The hydration level measurement method of claim 5 wherein said vessel identifier is an RFID tag.

8. The hydration level measurement method of claim 5 wherein said difference between said second weight and said first weight is measured in units selected from the group consisting of ounces, cups, milligrams, and grams.

9. The hydration level measurement system of claim 1 wherein said total point value associated with a user identifier comprises the sum of point values from a plurality of vessels associated with said user.

10. The hydration level measurement system of claim 1 wherein said users identifiers assigned to said challenge identifier are sorted according to challenge point totals for said challenge identifier.

11. The hydration level measurement system of claim 1 wherein:
  (a) said computer connected to said measuring device:
    (1) receives a start date and an end date associated with said at least one challenge identifier;
    (2) records total point values for users associated with said least one challenge identifier calculated on said start date;
    (3) determines a winner user identifier associated with said at least one challenge identifier with a highest total point value as of said end date; and
  (b) said display further displays said winner user identifier.

12. The hydration level measurement method of claim 5 wherein said total point value associated with said user identifier comprises a sum of point values from a plurality of vessels associated with said user identifier.

13. The hydration level measurement method of claim 5 wherein said users identifiers assigned to said at least one challenge identifier are displayed in a sorted order of user total point values.

14. The hydration level measurement method of claim 5 further comprising:
  (m) receiving at said computer a start date and an end date associated with said at least one challenge identifier;
  (n) recording at said computer total point values for users associated with said at least one challenge identifier on said start date;
  (o) determining at said computer a winner user identifier associated with said at least one challenge identifier a highest total point value recorded as of said end date; and
  (p) displaying at said computer said winner user identifier.

\* \* \* \* \*